United States Patent
Schell et al.

(10) Patent No.: US 10,090,914 B2
(45) Date of Patent: Oct. 2, 2018

(54) TEST PROBES FOR SMART INSPECTION

(71) Applicant: Fluke Corporation, Everett, WA (US)

(72) Inventors: J. David Schell, Austin, TX (US); Christian Schillab, Brunn am Gebirge (AT)

(73) Assignee: Fluke Corporation, Everett, WA (US)

( * ) Notice: Subject to any disclaimer, the term of this patent is extended or adjusted under 35 U.S.C. 154(b) by 298 days.

(21) Appl. No.: 14/882,304

(22) Filed: Oct. 13, 2015

(65) Prior Publication Data

US 2017/0104523 A1   Apr. 13, 2017

(51) Int. Cl.
| | |
|---|---|
| *H04N 7/18* | (2006.01) |
| *H04B 10/073* | (2013.01) |
| *G01B 9/04* | (2006.01) |
| *G01N 21/952* | (2006.01) |
| *G06K 9/00* | (2006.01) |
| *G01M 11/00* | (2006.01) |

(52) U.S. Cl.
CPC ............ *H04B 10/073* (2013.01); *G01B 9/04* (2013.01); *G01M 11/31* (2013.01); *G01N 21/952* (2013.01); *G06K 9/00* (2013.01)

(58) Field of Classification Search
CPC ........... G01M 11/31; G06K 9/00; G01B 9/04; G01N 21/952; H04B 10/073
USPC ......................................................... 348/135
See application file for complete search history.

(56) References Cited

U.S. PATENT DOCUMENTS

2008/0073485 A1 * 3/2008 Jahn ................... G01M 11/3154
                                                                  250/201.2
2013/0229650 A1 * 9/2013 Wilson ..................... B08B 1/00
                                                                  356/73.1

FOREIGN PATENT DOCUMENTS

| EP | 0740128 A2 * | 10/1996 | ........... G02B 6/3822 |
| WO | WO 03052348 A1 * | 6/2003 | ........... G01M 11/37 |
| WO | 2014184646 A1 | 11/2014 | |

* cited by examiner

*Primary Examiner* — Sathyanaraya V Perungavoor
*Assistant Examiner* — Peet Dhillon
(74) *Attorney, Agent, or Firm* — Seed IP Law Group LLP

(57) ABSTRACT

One or more embodiments are directed to apparatuses and methods of evaluating an endface of an optical communication link, such as a fiber optic cable. In at least one embodiment, a camera probe includes an imaging device that includes one or more feedback mechanisms, such as an alignment feedback mechanism that communicates alignment information regarding an alignment of the optical communication link under test with an image sensor of the camera probe. The alignment feedback mechanism may be visual and/or aural. The alignment feedback mechanism may provide directional information to the user indicative of a direction to move the imaging device relative to the optical communication link. In addition or alternatively, the feedback mechanism may include a focus feedback mechanism that communicates focus information regarding a focus of the endface in an obtained image of the endface.

20 Claims, 3 Drawing Sheets

TEST PROBES FOR SMART INSPECTION

BACKGROUND

Technical Field

The present disclosure generally pertains to inspections of optical communication links.

Description of the Related Art

Optical communication links, such as fiber optic cables, provide high speed transmission of data with relatively low loss. In view of this, optical communication links are often used in telecommunication networks, such as telephone lines, cable systems and the internet. In order to allow for adjustments to a network, such as adding, dropping, or moving optical cables in the network, or for coupling and decoupling to various transmitting and receiving equipment, each end of the fiber optic cables is held by a connector, such as a ceramic ferrule, a bulkhead adapter in a patch panel, etc., that allows for each of coupling and decoupling of the fiber optic cables. The connectors are designed to align the endfaces of optical fibers of two fiber optic cables to be coupled, and to abut the endfaces of the optical fibers of the fiber optic cables in physical contact with each other. The connectors also allow the endfaces of the optical fibers of fiber optic cables to be aligned with optical inputs and outputs of various transmitting and receiving equipment.

Performance of the fiber optic cables is affected by the integrity of the fiber optic cables and the quality of the connection between abutting fibers or other optical connections. Prior to coupling, tests, such as inline power tests, are performed on fiber optic cables to confirm that the cable satisfies appropriate standards. Additionally, visual inspections of endfaces may be performed to confirm the cleanliness of the endfaces of the optical fibers of the fiber optic cables prior to coupling. The integrity of the endfaces of the optical fibers of a fiber optic cable is of significant importance. For instance, contamination between abutting optical fibers of two abutting fiber optic cables may block, diffuse, or misdirect the optical signal traveling from optical fiber to another abutting optical fiber, thereby affecting the quality of the signal, such as reducing the intensity of the signal or introducing artifacts into the signal. Furthermore, contamination or defects on endfaces of optical fibers of a fiber optic cable may cause damage to endfaces of optical fibers of another fiber optic cable upon coupling of the two fiber optic cables.

A visual inspection process typically involves a camera probe that illuminates an endface of optical fibers of a fiber optic cable and obtains images of the endface. The inspection process may include a comparison to endface goodness standards for the intended application of the fiber optic cable. Such standards may be set by the International Electrotechnical Commission (IEC) (e.g., IEC Standard 61300-3-35) or various other organizations that set forth objective requirements for optical communication links, including Telecommunications Industry Association (TIA), Technical Standard Board (TSB), International Organization for Standardization (ISO), and Institute of Electrical and Electronic Engineers (IEEE).

BRIEF SUMMARY

Embodiments are directed to apparatuses, including test and camera probes, and methods of visually inspecting an endface of an optical communication link, such as a fiber optic cable.

One embodiment is directed to a test probe comprising an image sensor configured to obtain an image of an endface of an optical communication link and a display. The image sensor has a first field of view and display has a second field of view that is less than the first field of view of the image sensor. The test probe includes a processor operably coupled to the image sensor and the display. The processor is programmed to receive the obtained image from the image sensor, evaluate information that includes at least one of position information indicating a position of the endface in the obtained image relative to the second field of view and focus information indicating a focus of the endface in the obtained image, and generate one or more signals indicative of the information. The test probe further includes a feedback mechanism operably coupled to the processor and configured to receive the one or more signals indicative of the information and to provide at least one of an aural and visual indication of the information to a user.

Another embodiment is directed to a camera probe comprising an imaging device and an analysis device operably coupled to the imaging device. The imaging device includes an image sensor configured to obtain an image of an endface of an optical communication link and an alignment feedback mechanism configured to communicate information regarding an alignment of the endface in the obtained image in response to one or more signals received from a processor. The analysis device includes a processor and a display having a field of view. The processor is programmed to receive the obtained image from the image sensor, identify the endface in the obtained image, determine a location of the endface in the obtained image relative to the field of view of the display, and generate one or more signals indicative of the location of the endface in the obtained image relative to the field of view of the display and provide the one or more signals to the alignment feedback mechanism.

Another embodiment is directed to a method comprising obtaining an image of an endface of an optical communication link from an image sensor having first field of view. The obtained image is displayable on a display having a second field of view that is less than the first field of view. The display shows a portion of the obtained image in the second field of view. The method further includes identifying the endface in the obtained image in the first field of view and determining whether the endface identified in the obtained image is located outside the portion of the obtained image shown in the second field of view. The method further includes indicating to a user when the endface identified in the obtained image is located outside the portion of the obtained image shown in the second field of view.

DETAILED DESCRIPTION

Figure 1:
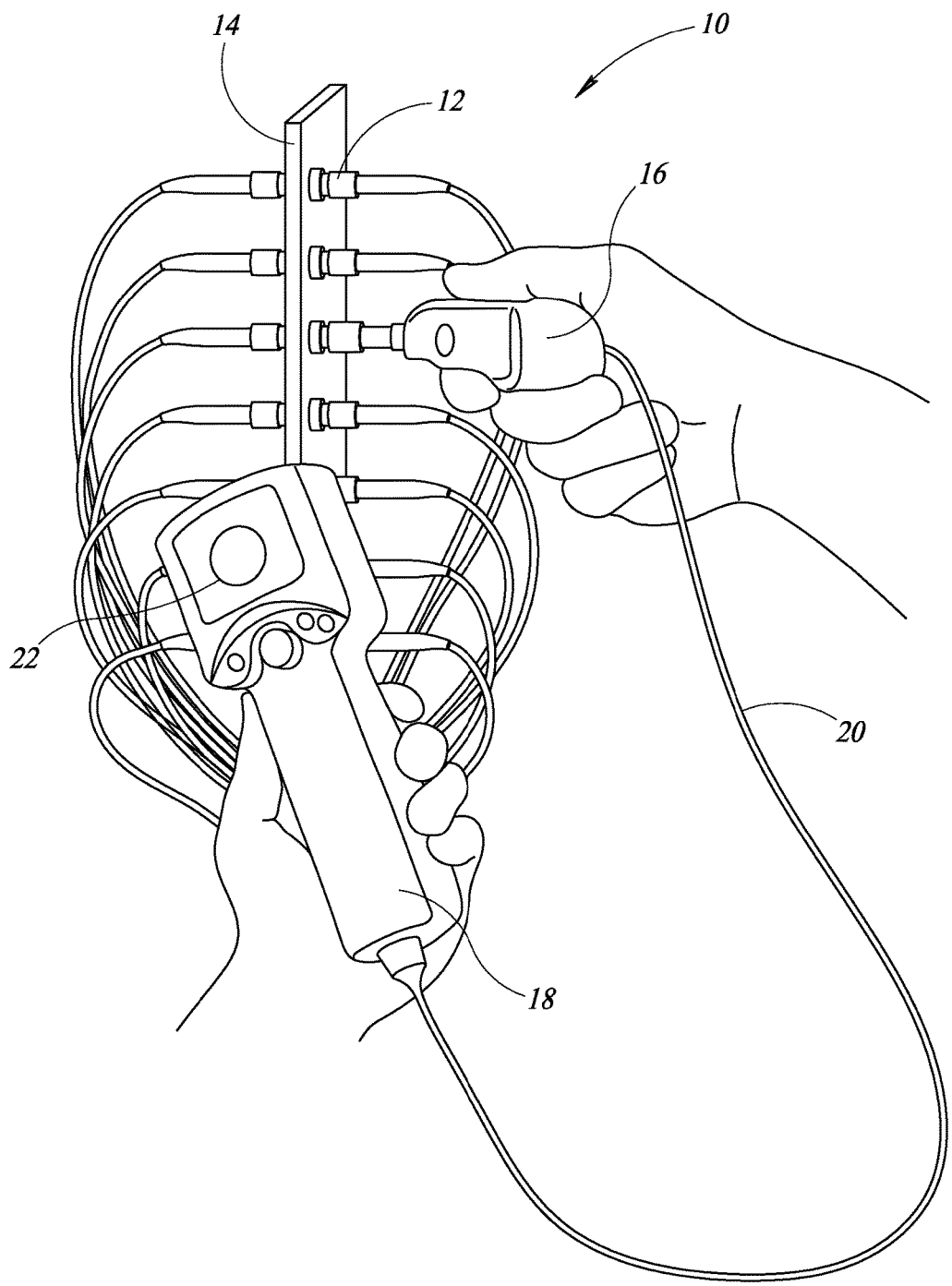
FIG. 1 is an illustration of a known camera probe being used with a bulkhead adapter at a patch panel.

Testing, such as visual inspection or inline power testing, of optical communication links can be cumbersome, particularly when the testing occurs at patch panels. FIG. 1 illustrates a user using a known camera probe 10 to inspect fiber optic cables via bulkhead adaptors 12 at a patch panel 14. The camera probe 10 includes an imaging device 16 that is operably coupled to an analysis device 18 by a wire 20. The imaging device 16 is configured to obtain images of endfaces of fiber optic cables that include fiber optics being inspected and the analysis device 18 is configured to receive, analyze, and display the obtained images.

In general, the imaging device 16 is configured to couple with various connectors, including ceramic ferrules and bulkhead adapters. This flexibility of being able to couple the imaging device 16 with various connectors limits the ability of the imaging device 16 to auto-align with the endfaces of the fiber optic cables being inspected. Instead, a user typically holds and adjusts the imaging device 16 in one hand to orientate an image sensor therein with the endface under test. In particular, the imaging device 16 may be rotated, pivoted, slid or any other movement relative to the endface of the fiber optic cable in order to suitably align the image sensor with the endface.

To determine that a suitable alignment has been reached, the user refers to a display 22 of the analysis device 18, which is often held in the user's other hand, such as is shown in FIG. 1. Thus, while the user is adjusting the alignment of the imaging device 16 relative to the endface of the fiber optic cable, the user is looking at the display 22 in the other hand, which can be awkward and take some time for a user to get used to. Furthermore, minor adjustments made to the orientation of the imaging device 16 can cause the endface to move quickly on and off the display of the analysis device 18. In that regard, aligning the imaging device 16 with the endface so that the endface is suitably displayed on the display of the analysis device 18 can take some time and expertise. Furthermore, the alignment process can be even more awkward and cumbersome when the connector of the fiber optic cable under test provides limited access for the user.

One or more embodiments disclosed herein are directed to test probes, such as camera probes or inline power test probes, for testing optical communication links. The test probes include an imaging device for obtaining images of the optical communication link under test. The imaging device includes one or more feedback mechanisms configured to provide information to a user regarding the images obtained by the imaging device.

In various embodiments, the feedback mechanism includes an alignment feedback mechanism that provides information to the user regarding the alignment of the imaging device with the optical communication link under test. The alignment information may be information regarding the proximity of the endface in the obtained image relative to a display's field of view, a direction at which the endface is located, a direction to move the imaging device relative to the endface, or any other information regarding the alignment of the endface. Separately or in addition, the feedback mechanism may also include a focus feedback mechanism that provides information to the user regarding the focus of the image of the optical communication link under test. The feedback mechanism may provide the information to the user visually and/or audibly.

Figure 2:
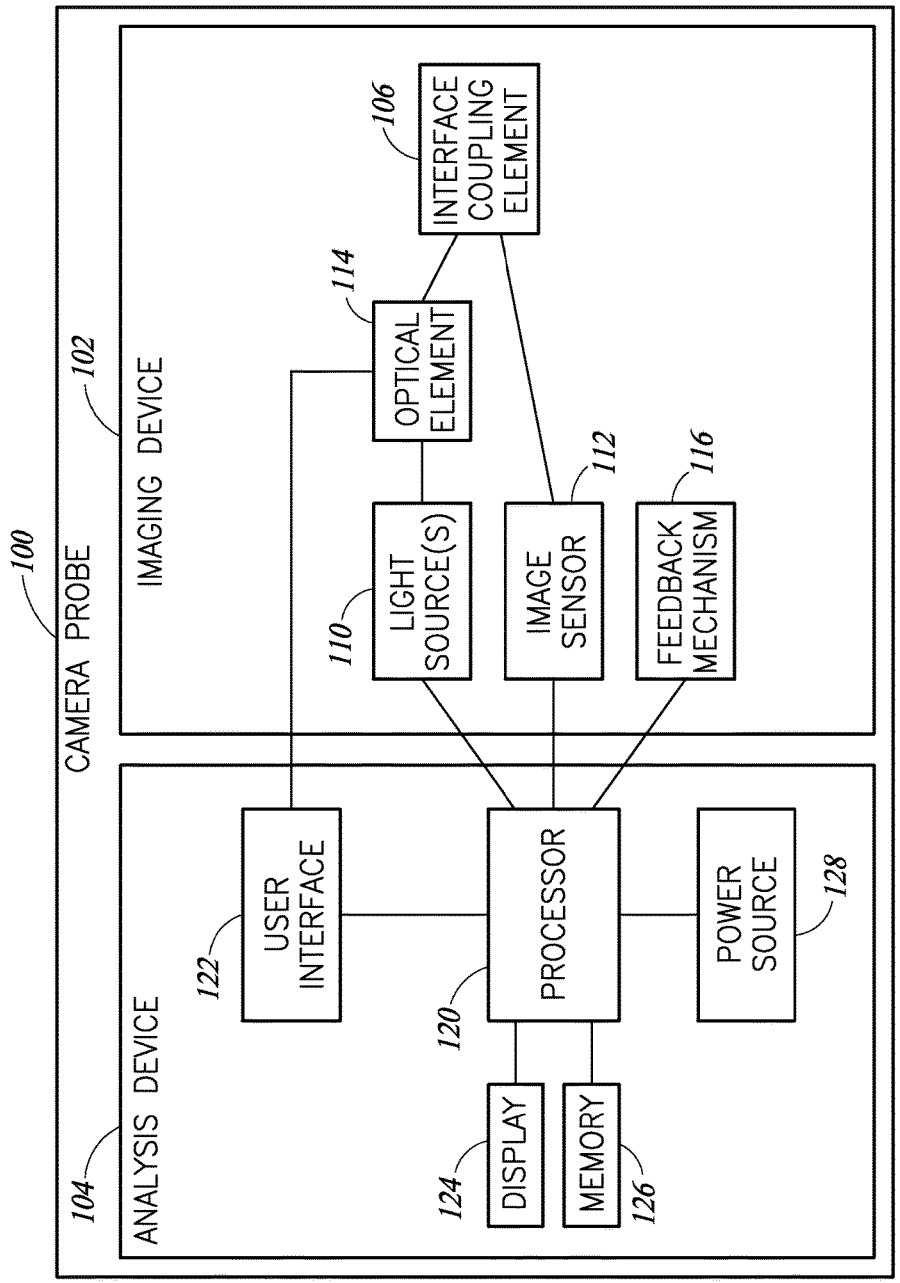
FIG. 2 is a block diagram illustrating a camera probe according to an embodiment of the disclosure.

FIG. 2 illustrates a block diagram of a test probe or camera probe 100 for inspecting endfaces of optical communication links, such as fiber optic cables, in accordance with an embodiment of the present disclosure. The camera probe 100 includes an imaging device 102 for obtaining images of an endface of a fiber optic cable (not shown) to be inspected. The imaging device 102 is operably coupled to an analysis device 104 configured to receive and display the images obtained by the imaging device 102.

The imaging device 102 includes an interface coupling element 106 configured to mate with various connectors, such as a ceramic ferrule, a bulkhead adapter in a patch panel, etc., of a fiber optic cable to be inspected. The interface coupling element 106 may be configured to mate with the connectors in various ways, such as by male-to-female coupling, or may include a separable adaptor for coupling to different connectors.

The imaging device 102 includes one or more light sources 110, such as a light emitting diode (LED), that project light through the interface coupling element 106 and illuminate the endface of the fiber optic cable 106 under test. The imaging device 102 further includes an image sensor 112 for obtaining images of the endface of the fiber optic cable 106 under test. As indicated above, the imaging device 102 is operatively coupled to the analysis device 104 and provides the images of the endface obtained by the image sensor 112 to the analysis device 104.

The imaging device 102 may further include one or more optical elements 114, such as focusing lenses, prisms, and mirrors, arranged in the cavity 108. The prisms and mirrors may be used to direct light from the light source 110 to the interface coupling element 106. The focusing lenses are configured to focus the image sensor 112 with the endface under test. The one or more optical elements 114 may be coupled to a user interface, such as a knob, on the body of the imaging device 102 or to a user interface 122 of the analysis device 104. In that regard, the imaging device 102 may provide for manual focus of the endface under test by adjusting of a knob on the imaging device 102 or the analysis device 104.

The imaging device 102 further includes a feedback mechanism 116 that is configured to communicate information to the user. The information may include information regarding the alignment of the imaging device 102 relative to an endface of a fiber optic cable under test and/or the focus of the image of the endface, as will be explained in more detail below.

The analysis device 104 includes a processor 120 operably coupled to the light source 110, image sensor 112, and feedback mechanism 116 of the imaging device 102. The processor 120 includes suitable programming logic operable to activate and deactivate the light source 110 and to operate the image sensor 112. The processor 120 is configured receive imaging data of images obtained from the image sensor 112 and includes suitable programming logic to process the imaging data. The processor 120 is configured to store the imaging data received from the image sensor 112 in the memory 126 and to cause a display to display images of the endface of the fiber optic cable under test. The processor 120 further includes suitable programming logic to generate and provide signals indicative of information, such as alignment information or focus information, to be communicated to a user by the feedback mechanism 116 as referred to above.

The processor 120 is further coupled a user interface 122, a display 124, a memory 126, and a power source 128 of the analysis device 108. The display 124 is configured to display the images obtained by the image sensor 112. In general, however, the display 124 has a field of view that is less than a field of view of the image sensor 112. In that regard, even if the image sensor 112 is obtaining an image of the endface of the fiber optic cable under test, the display 124 may not be displaying the portion of the image that includes the endface. That is, the endface may be outside of the field of view of the display 124, while inside the field of view of the image sensor 112.

The processor 120 of the analysis device 104 includes suitable programming logic to detect when the endface is inside the field of view of the image sensor 112, but outside of the field of view of the display 124. The processor 120 is configured to communicate signals to the feedback mechanism 116 indicative of this discrepancy. For instance, the feedback mechanism 116 may indicate a proximity of the endface in the obtained image relative to the display's 124 field of view, a direction to move the imaging device 102, a location of the endface relative to the field of view of the display 124, or any other suitable information that communicates to the user information regarding the alignment of the imaging device 102 with the optical communication link under test.

The signals generated by the processor 120 indicative of alignment of the endface are provided to the feedback mechanism 116 for communicating to the user. As indicated above, the feedback mechanism 116 may be a visual feedback mechanism that visually communicates information regarding the alignment of the endface relative to field of view of the display 124. For instance, a visual feedback mechanism may include a display, a gauge, or any other visual indicator. Additionally, or alternatively, the feedback mechanism 116 may be audio in which audible signals indicate the information.

In one embodiment, the processor 120 is able to detect the endface by identifying a dark spot in the obtained image that is indicative of an endface. More particularly, the processor 120 may be operable to identify a cluster of pixels above a threshold size that are above a threshold gray scale value indicative of the endface under test. The location of the dark spot is further compared with the field of view of the display 124 to determine whether the dark spot is within or outside of the field of view of the display 124. The processor 120 is further configured to determine information regarding the dark spot and the field of view of the display 124, such as a location, direction and proximity of the dark spot relative to the display's field of view.

When the endface is detected to be outside of the field of view of the display 124, the processor 120 is configured to generate signals indicative of information determined during the analysis and provide the generated signals to the feedback mechanism 116 for communication to the user. In that regard, the processor 120 may provide signals indicative of the proximity, location, direction, or any other useful alignment information of the detected dark spot relative to the field of view of the display 124. When the endface is detected to be within the field of view of the display 124, the processor 120 is configured to generate signals indicating that alignment has been reached and provide the generated signals to the feedback mechanism 116 for communication to the user.

Similarly, the processor 120 may include suitable programming logic to determine when the obtained images of the endface under test have a focus and/or contrast within a particular range. For instance, the processor 120 may be configured to compare at least a portion of the obtained image with a stored image in order to determine that the focus and/or contrast of the endface is within a suitable range. When the focus and/or contrast are determined to be within a particular range, the processor 120 provides a signal to the feedback mechanism 116 indicative that suitable focus and/or contrast has been achieved. In another embodiment, the focus may be determined by analyzing the sharpness of edges detected in the obtained image and comparing the sharpness to a threshold. The contrast may be determined by comparing the gray scale of various portions of the obtained image with a stored image. When the focus is determined to be outside the particular range, the processor 120 is configured to determine a direction at which one or more optical elements 114 may be moved in order to obtain suitable focus of the endface. The processor 120 may generate signals indicative of the direction or a direction to move a user interface 122, for example a knob, and provide the signals to the feedback mechanism 116 for communication to the user.

Upon determining that an image meets suitable ranges for focus and/or contrast, the processor 120 may be configured to obtain and store the image without requiring input from the user. That is, the processor 120 is configured to activate the image sensor 112 to capture an image in response to determining that at least one of the focus and contrast are within a particular range and cause the obtained image to be stored in the memory 126 without receiving instructions from the user via the user interface 122. When saving the obtained image or after saving the obtained image, processor may be configured to further label the obtained image to indicate the image has contrast and/or focus within a preferred range. Additionally, the processor 120 may be configured to obtain a power measurement in response to determining that at least one of the focus and contrast are within a particular range without receiving instructions from the user via the user interface 122.

As will be clear to a person of ordinary skill in the art, the feedback mechanism 116 may provide a different indication regarding alignment than is provided for focus. For instance, the alignment feedback mechanism may be visual and the focus feedback mechanism may be aural or vice versa.

The user interface 122 of the analysis device 104 may include the display, keyboard, knobs, and buttons that allow a user to interact with the processor 120, such as to cause the processor 120 to activate or deactivate the light source 110 or to capture an image of the endface of the fiber optic cable under test, or to operate other components of the camera probe.

The power source 128, which can be a battery or a plug for coupling to a main power supply, provides power for operating the camera probe 100. Although FIG. 2 shows the camera probe 100 as a single unit, it is to be appreciated that the imaging device 102 and the analysis device 104 may be separate components that are coupled together by a wire or wirelessly coupled. As separate components, the imaging device 102 may include its own power source or may be powered by the analysis device 104.

Figure 3A:
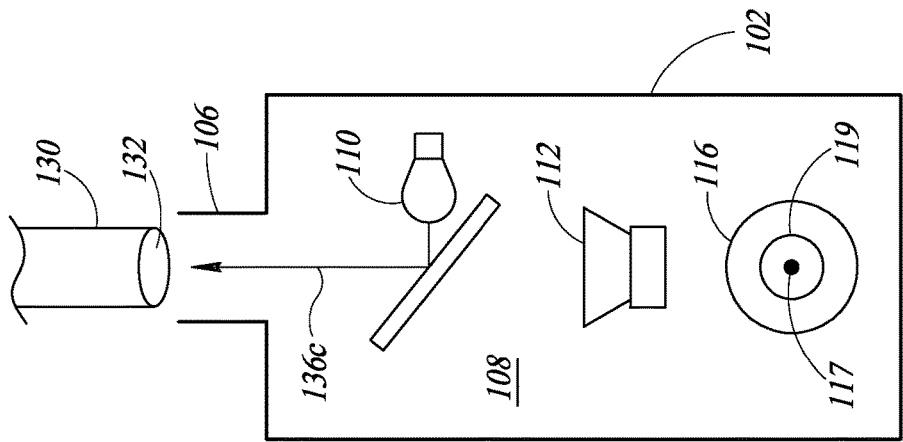
FIGS. 3A-3C are schematic illustrations of an imaging device of a camera probe in accordance with an embodiment of the disclosure.
Figure 3B:
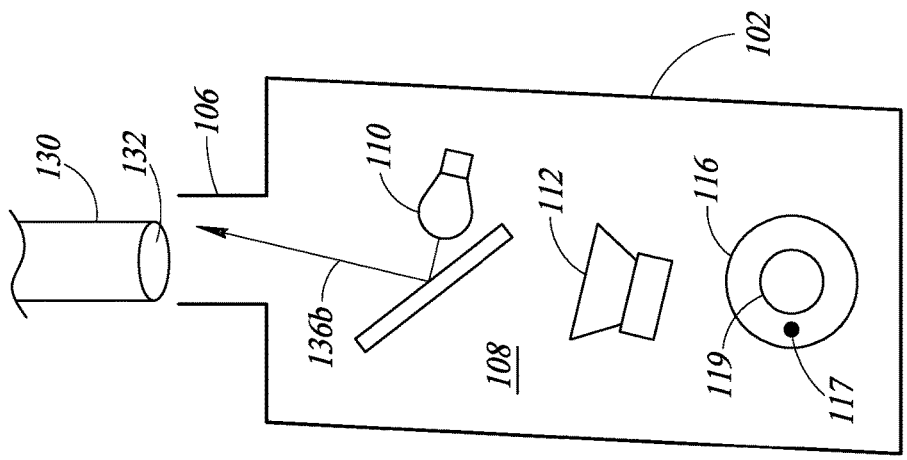
Figure 3C:
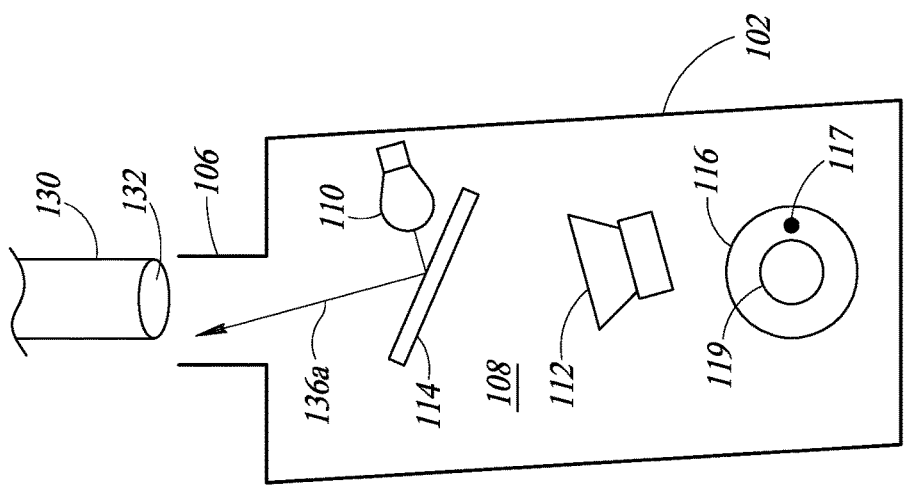

FIGS. 3A-3C are schematic illustrations of the imaging device 102 of the camera probe 100 in various positions relative to an endface 132 of a fiber optic cable 130 under test. As will be clear to person of ordinary skill in the art, the orientation of the imaging device 102 in FIGS. 3A-3C is exaggerated to more clearly illustrate the alignment process.

As shown in FIGS. 3A-3C, the light source 110 is arranged in a cavity 108 to project light toward the optical element 114, such as a mirror, for reflecting light 136*a* through the interface coupling element 106 to an endface 132 of a fiber optic cable 130 under test. The image sensor 112 is arranged in the cavity 108 to obtain images of the endface 132.

The feedback mechanism 116 is located on an outer surface of the imaging device 102 and is a visual feedback mechanism for communicating information regarding alignment of the imaging device 102 with the endface 132 under test. In particular, the feedback mechanism 116 indicates information regarding the location of the endface 132 relative to the field of view of the display 124 of FIG. 1 as discussed above.

FIG. 3A illustrates the imaging device 102 orientated such that the endface 132 is within the image sensor's 112 field of view but outside of the field of view of the display 124. In particular, the endface 132 is located to the right of the field of view of the display 124. Thus, the display 124 of the analysis device 104 would not display the endface 132 to the user. Even though the display 124 of the analysis device is not displaying the endface 132 to the user, the user is able to refer to the alignment feedback mechanism 116 to determine which direction to move, such as rotate, pivot, slide, etc., the imaging device 102 relative to the endface 132 in order to place the endface 132 within the field of view of the display 124.

In the illustrated embodiment, a dark circle 117 is representative of the endface 132 obtained by the image sensor 112 and a circle 119 is representative of the field of view of the display 124. Thus, the feedback mechanism 116 of FIG. 3A communicates a location of the endface 132 relative to the field of view of the display 124, a direction to move the imaging device 102 in order to get the endface 132 within the display's field of view, and the proximity of the endface 132 relative to the display's field of view. It is to be appreciated that the feedback mechanism 116 may alternatively communicate only one or two of these indications, or communicate any other useful alignment information to the user.

Based on the information provided by the feedback mechanism 116, the user would move the imaging device 102, such as to pivot the imaging device 102 to the left, to align the endface 132 with the field of view of the display 124. Without the alignment feedback mechanism 116, the user would not know which way to move the imaging device 102 in order to get the endface 132 within the field of view of the display 124.

FIG. 3B illustrates the imaging device 102 having been pivoted, but pivoted too far to the left so that the endface 132 is again within the image sensor's field of view but outside of the field of view of the display 124. Again, the display 124 of the analysis device 104 would not display the endface 132 to the user. Rather, the user refers to the feedback mechanism 116, which places the dark circle 117 indicative of the endface 132 outside the circle 119, which is indicative of the field of view of the display 124. Thus, the user only knows the location of the endface 132 relative to the display's field of view due because of the feedback mechanism 116. Based on the information provided by the feedback mechanism 116, the user knows to move or pivot the imaging device 102 to the right.

FIG. 3C illustrates the imaging device 102 orientated such that the endface 132 is within the field of view of the display 124. The feedback mechanism 116 communicates that the endface 132 is within the display's field of view to the user by placing the dark circle 117 inside of the circle 119. Thus, the user knows, based on the feedback mechanism 116, that the display 124 is displaying an image of the endface 132. It is to be appreciated that further processing of the images may be performed. For instance, the processor may include programming logic to center the endface 132 once alignment has been reached. The illustrated feedback mechanism 116 may be a display, a gauge, or any other suitable visual communication element.

Alternatively, the feedback mechanism 116 may be an audible feedback mechanism. In that regard, the feedback mechanism 116 may be a speaker on the imaging device 102 that provides different types of sounds indicative of the information regarding the alignment information as discussed above. For instance, as endface 132 moves closer to the display's 124 field of view, an audible feedback mechanism may output sounds that are higher pitched, sound pulses may become more closely spaced together, a combination thereof, or any other audible communication. Conversely, when the endface 132 moves toward an outer periphery of the image sensor's 112 field of view and, thus, farther from the display's 124 field of view, the audible signals may become lower pitched, farther spaced apart, a combination thereof, or any other distinctive audible communication.

As indicated above, the feedback mechanism 116 may be configured to communicate information regarding the focus of the endface 132. A feedback mechanism that provides focus information may be separate structure from a feedback mechanism that provides alignment information. For instance, in one embodiment the feedback mechanism 116 for focus is a speaker that provides audio signals to the user, while the feedback mechanism 116 for alignment is a display or gauge that provides visual signals to the user, or vice versa. For example, when the focus is determined to be outside a particular range, the feedback mechanism for focus may indicate a direction for the user to move one or more optical elements 114 in order to obtain suitable focus of the endface.

While the foregoing description illustrates and describes a camera probe for visually inspecting an endface of a communication link, it should be understood that the disclosure is directed to any test probes, such as test probes for testing inline power and/or loss measurements, that may benefit from improved alignment of optical communication links prior to test. Furthermore, although only a single processor is shown and described, it should be understood that other circuitry may be coupled to the processor or other components in the camera probe to perform the programming logic described herein.

The various features and embodiments described above can be combined in any manner to provide further embodiments. These and other changes can be made to the embodiments in light of the above-detailed description. In general, in the following claims, the terms used should not be construed to limit the claims to the specific embodiments disclosed in the specification, but should be construed to include all possible embodiments along with the full scope of equivalents to which such claims are entitled. Accordingly, the claims are not limited by the specific embodiments disclosed.

The invention claimed is:

1. A test probe comprising:
   an image sensor configured to obtain an image of an endface of an optical communication link, the image sensor having a first field of view;
   a display having a second field of view that is less than the first field of view of the image sensor;
   a processor operably coupled to the image sensor and the display, the processor programmed to:
      receive the obtained image from the image sensor,
      evaluate information that includes position information indicating a position of the endface in the obtained image relative to the second field of view, and
      generate one or more signals indicative of the position information; and
   a feedback mechanism operably coupled to the processor and configured to receive the one or more signals indicative of the position information and to provide at least one of an aural and visual indication of the position information to a user.

2. The test probe of claim 1, wherein the position information includes at least one of a proximity of the endface in the obtained image relative to the second field of view, a direction at which the endface is located relative to the second field of view, and a direction to move the image sensor relative to the endface.

3. The test probe of claim 1, further comprising a user interface operably coupled to an optical element, wherein the information further includes focus information indicating a focus of the endface in the obtained image, wherein the focus information includes a direction to adjust the user interface that causes the optical element to move in order to obtain an improved focus of the endface in the obtained image.

4. The test probe of claim 1, wherein the processor is programmed to perform a grayscale analysis of pixels of the obtained image to identify the endface in the obtained image.

5. The test probe of claim 1, wherein the feedback mechanism visually illustrates the position information of the endface relative to the second field of view.

6. The test probe of claim 1, wherein the image is a first image and wherein the position is a first position, wherein the image sensor is configured to obtain a second image of the endface of the optical communication link and the processor is programmed to:
receive the second image from the image sensor,
evaluate updated position information that includes position information indicating a second position of the endface in the second image relative to the second field of view, and
generate one or more signals indicative of the updated position information.

7. The test probe of claim 6, wherein the feedback mechanism is a speaker that outputs signals with at least one of a pitch or pulse indicative of least one of the position information of the endface relative to the second field of view.

8. A camera probe comprising:
an imaging device including an image sensor configured to obtain an image of an endface of an optical communication link, the imaging device further including an alignment feedback mechanism configured to communicate information to a user in response to one or more signals received from a processor; and
an analysis device operably coupled to the imaging device and including a processor and a display having a field of view, wherein the processor is programmed to:
receive the obtained image from the image sensor;
identify the endface in the obtained image;
determine a location of the endface in the obtained image relative to the field of view of the display; and
generate one or more signals indicative of the location of the endface in the obtained image relative to the field of view of the display and provide the one or more signals to the alignment feedback mechanism, wherein the information includes a direction to move the camera probe to cause the display to display the endface.

9. The camera probe of claim 8, wherein the alignment feedback mechanism provides a visual indication of the alignment of the endface relative to the field of view of the display.

10. The camera probe of claim 9, wherein the processor is programmed to perform a grayscale analysis of pixels of the obtained image to identify the endface in the obtained image.

11. The camera probe of claim 8, wherein the alignment feedback mechanism is a speaker configured to provide audible signals indicating the alignment of the endface relative to the field of view of the display.

12. The camera probe of claim 8, wherein the location of the endface the obtained image relative to the field of view of the display includes at least one of information regarding a proximity of the endface in the obtained image relative to the field of view of the display, a direction at which the endface is located relative to the field of view of the display, and a direction to move the imaging device relative to the endface.

13. The camera probe of claim 8, wherein the image is a first image and wherein the position is a first position, wherein the image sensor is configured to obtain a second image of the endface of the optical communication link and the processor is programmed to:
receive the second image from the image sensor,
evaluate updated information that includes position information indicating a second position of the endface in the second image relative to the second field of view, and
generate one or more signals indicative of the updated information.

14. A method comprising:
obtaining an image of an endface of an optical communication link from an image sensor having first field of view, wherein the obtained image is displayable on a display having a second field of view that is less than the first field of view, the display showing a portion of the obtained image in the second field of view;
identifying the endface in the obtained image in the first field of view;
determining whether the endface identified in the obtained image is located outside the portion of the obtained image shown in the second field of view; and
indicating to a user when the endface identified in the obtained image is located outside the portion of the obtained image shown in the second field of view.

15. The method of claim 14, wherein indicating to the user includes providing a signal to a display to visually indicate that the endface identified in the obtained image is located outside the portion of the obtained image shown in the second field of view.

16. The method of claim 15, wherein determining whether the endface identified in the obtained image is located outside the portion of the obtained image shown in the second field of view further includes determining at least one of a proximity, a direction, and a location of the endface relative to the portion of the obtained image shown in the second field of view.

17. The method of claim 15, wherein indicating to the user comprises generating an audible signal indicative of a proximity of the endface identified in the obtained image relative to the portion of the obtained image shown in the second field of view.

18. The method of claim 15, wherein indicating to the user provides a first indication, and wherein when the endface identified in the obtained image is located inside the portion of the obtained image shown in the second field of view, the method comprises providing a second indication to the user different from the first indication.

19. The method of claim 15, further comprising moving the image sensor relative to the endface.

20. The method of claim 15, wherein the image is a first image and wherein the position is a first position, the method further comprising:
- obtaining a second image of the endface, the display showing a portion of the obtained second image in the second field of view;
- identifying the endface in the second image in the first field of view;
- determining whether the endface identified in the second image is located outside the portion of the obtained second image shown in the second field of view; and
- indicating to the user when the endface identified in the obtained second image is located outside the portion of the obtained second image shown in the second field of view.

\* \* \* \* \*